DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED FEBRUARY 23, 1971

884 O.G. 1323

T883,022

PREPARATION OF AMMONIUM 1,4-CYCLOHEXANEDICARBOXYLATE

Thomas H. Strickland and Charles J. Kibler, both of P.O. Box 511, Kingsport, Tenn. 37662

Continuation of application Ser. No. 565,412, July 15, 1966. This application Dec. 19, 1969, Ser. No. 4,158

Int. Cl. C07c *51/36*

U.S. Cl. 260—514

No Drawing. 5 Pages Specification

Ammonium 1,4-cyclohexanedicarboxylate is prepared by hydrogenating terephthalic acid in the presence of an excess of ammonium hydroxide over pladium catalysts. Ammonium 1,4-cyclohexanedicarboxylate is a valuable chemical intermediate, e.g., in the synthesis of polyamides.